US010098611B2

(12) United States Patent
Lee et al.

(10) Patent No.: US 10,098,611 B2
(45) Date of Patent: Oct. 16, 2018

(54) WEARABLE AND NON-WEARABLE ELECTRONIC STETHOSCOPES AND USE OF THE DIGITIZED ACOUSTIC DATA FOR DATA ANALYTICS AND HEALTHCARE

(71) Applicant: International Business Machines Corporation, Armonk, NY (US)

(72) Inventors: Kang-Wook Lee, Yorktown Heights, NY (US); John U. Knickerbocker, Orange County, NY (US)

(73) Assignee: International Business Machines Corporation, Armonk, NY (US)

( * ) Notice: Subject to any disclaimer, the term of this patent is extended or adjusted under 35 U.S.C. 154(b) by 305 days.

(21) Appl. No.: 14/977,855

(22) Filed: Dec. 22, 2015

(65) Prior Publication Data

US 2017/0172537 A1 Jun. 22, 2017

(51) Int. Cl.

*A61B 7/04* (2006.01)
*A61B 7/00* (2006.01)

(52) U.S. Cl.

CPC ................ *A61B 7/04* (2013.01); *A61B 7/003* (2013.01)

(58) Field of Classification Search

CPC ........ A61B 7/04; A61B 7/003; A61B 2503/40
See application file for complete search history.

(56) References Cited

U.S. PATENT DOCUMENTS 6,139,505 A * 10/2000 Murphy ................. A61B 5/061 381/67
6,498,854 B1 12/2002 Smith
6,527,729 B1 3/2003 Turcott
6,661,897 B2 12/2003 Smith
7,424,929 B1 * 9/2008 Martinez .................. A61B 7/02 181/131
7,724,147 B2 5/2010 Brown
8,197,431 B2 6/2012 Bennison
2001/0041845 A1 * 11/2001 Kim ..................... A61B 5/6887 600/528
2002/0071570 A1 * 6/2002 Cohen ..................... A61B 7/04 381/67
2004/0100376 A1 5/2004 Lye et al.
2005/0033144 A1 * 2/2005 Wada ..................... A61B 7/003 600/407

(Continued)

OTHER PUBLICATIONS

Highly Stretchable Resistive Pressure Sensors Using a Conductive Elastomeric Composite on a Micropyramid Array, Choong et al., Advanced Materials, 26, 3451-3458.*

(Continued)

*Primary Examiner* — Sean Dougherty
(74) *Attorney, Agent, or Firm* — Harrington & Smith; Louis J. Percello

(57) ABSTRACT

In accordance with the example embodiments of the invention there is at least a method and apparatus to perform receiving, with at least one diaphragm of a device placed on a skin of a living body of a human being or animal, acoustic data of the living body; determining digitized data from the acoustic data of the living body; and sending the digitized data towards an analytics system for a medical diagnosis associated with the living body; determining a relationship between the digitized data and health conditions of the human being or animal; and applying the relationship to a diagnosis of the health conditions of the human being or animal.

18 Claims, 8 Drawing Sheets

(56) References Cited

U.S. PATENT DOCUMENTS

| | | | | |
|---|---|---|---|---|
| 2006/0018487 | A1 | 6/2006 | Smith | |
| 2008/0114266 | A1* | 5/2008 | Shen | A61B 7/003<br>600/586 |

OTHER PUBLICATIONS

Tunable Flexible Pressure Sensors using Microstructured Elastomer Geometries for Intuitive Electornics, Tee et al., Advanced Functional Materials, 2014, 24, 5427-5434.*

Ko, JeongGil, et al., "Wireless Sensor Networks for Healthcare", IEEE, vol. 98, No. 11, Nov. 2010, pp. 1947-1960.

Patel, Shyamal, et al., "A review of wearable sensors and systems with application in rehabilitation", Journal of NeuroEngineering and Rehabilitation, 2012, 17 pgs.

* cited by examiner

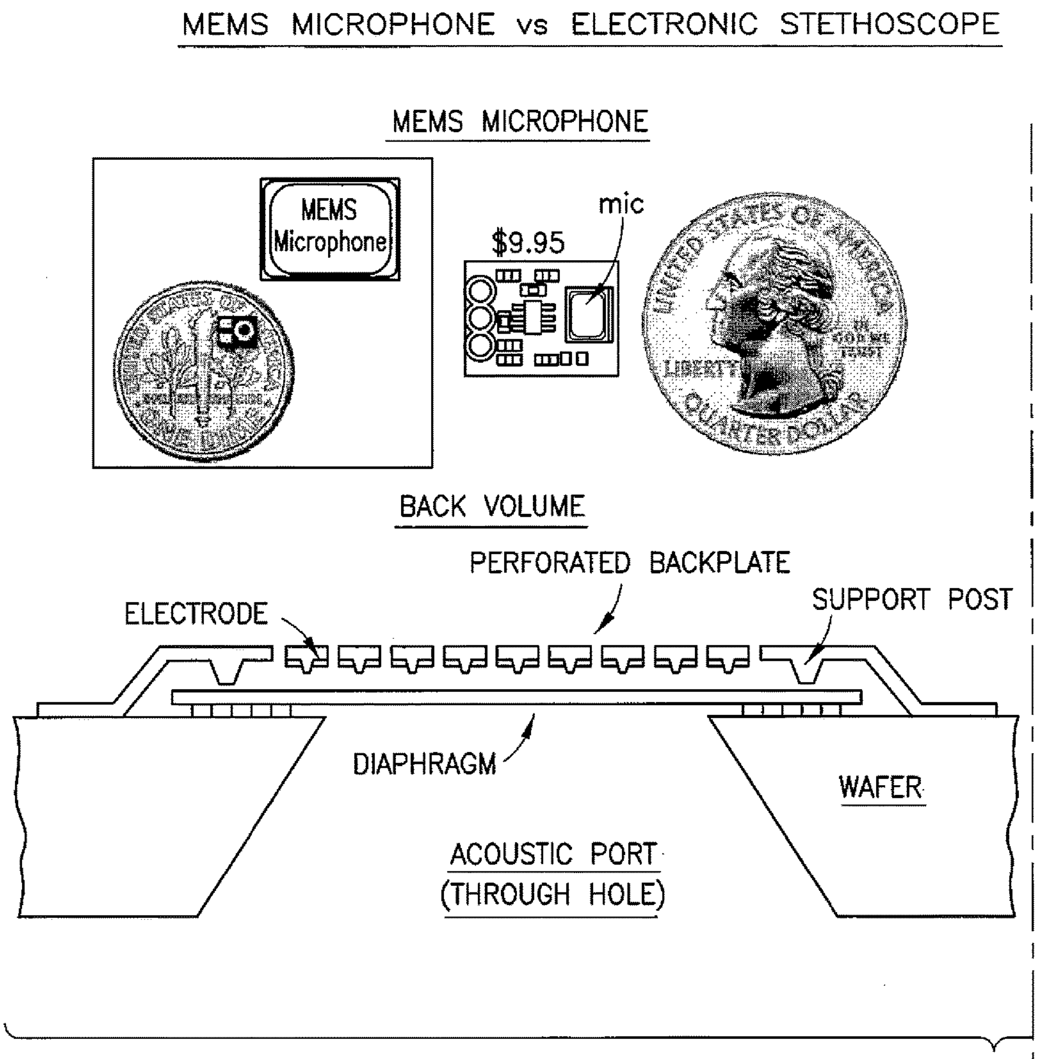
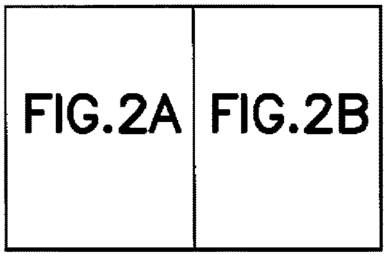
FIG.2
FIG.2A

Conventional Electronic Stethoscope

Conventional electronic stethoscope

2: diaphragm
4: thin metal conductor
3: metal conductor plate
5: Mylar (polymer film)
7: air or liquid (>100 um gap)
1 & 6: housing (Cr-coated Al)
9: Diaphragm mount
10, 11 & 13: Electronic Circuitry
14: wire to a battery

Wireless Electronic Stethoscope

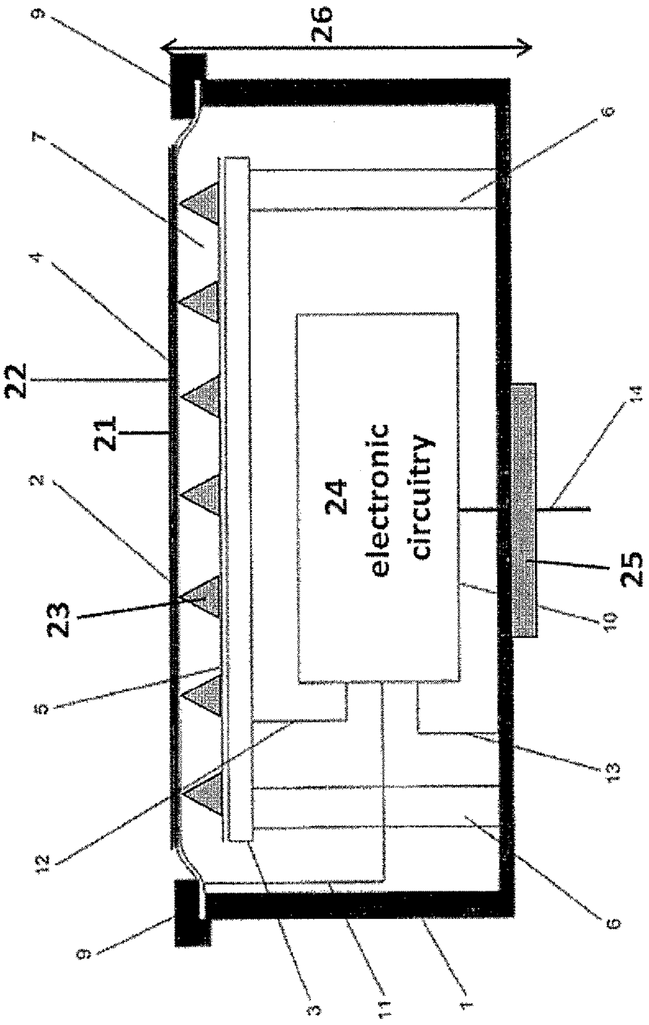

Wireless electronic stethoscope

2: diaphragm
4: thin metal conductor
3: metal conductor plate
5: Mylar (polymer film)
7: air or liquid
1 & 6: housing (Cr-coated Al)
14: wire to a battery
21: bio-compatible pressure adhesive
22: thin polymer film
23: elastomeric pyramids (5-20 um gap)
24: capacitance measurement, capacitance to digital converter, amplifier, RF
25: battery
26: thinner stethoscope

FIGURE 3B

WEARABLE AND NON-WEARABLE ELECTRONIC STETHOSCOPES AND USE OF THE DIGITIZED ACOUSTIC DATA FOR DATA ANALYTICS AND HEALTHCARE

TECHNICAL FIELD

The teachings in accordance with the exemplary embodiments of this invention relate generally to wearable and non-wearable electronic stethoscopes and, more specifically, relate to wearable and non-wearable electronic stethoscopes with an improved configuration for listening to acoustic data of a body.

BACKGROUND

Auscultation (based on the Latin verb auscultare “to listen”) is known as a process of listening to the internal sounds of the body and has historically been performed with stethoscopes. Auscultation is performed for the purposes of examining body systems such as the circulatory and respiratory systems such as to listen to heart and breath sounds, as well as the gastrointestinal system or bowel sounds.

In addition, healthcare costs continue to increase, and U.S. healthcare cost are approximately $2.5 T per year. If 10% of the cost comes from regular checkups by primary physicians, its cost will be $250 B in the US and $1 T in the world. The analytics of health data from health sensors can decrease the healthcare cost in an individual level and in a world level. The example embodiments of the invention as described below at least provide a novel stethoscope with an improved design which can communicate health care data with healthcare analytics systems in order to interpret the health care data and provide real-time healthcare monitoring, early diagnosis, and warnings.

SUMMARY

In an exemplary aspect of the invention, there is a method comprising: receiving, with at least one diaphragm of a device placed on a skin of a living body of a human being or animal, acoustic data of the living body; determining digitized data from the acoustic data of the living body; sending the digitized data towards an analytics system for a medical diagnosis associated with the living body; determining a relationship between the digitized data and health conditions of the human being or animal; and applying the relationship to a diagnosis of the health conditions of the human being or animal.

In another exemplary aspect of the invention, an apparatus comprising: at least one processor; and at least one memory including computer program code, where the at least one memory and the computer program code are configured, with the at least one processor, to cause the apparatus to at least: receive, with at least one diaphragm of the apparatus placed on a skin of a living body of a human being or animal, acoustic data of the living body; determine digitized data from the acoustic data of the living body; send the digitized data towards an analytics system for a medical diagnosis associated with the living body; determine a relationship between the digitized data and health conditions of the human being or animal; and apply the relationship to a diagnosis of the health conditions of the human being or animal.

BRIEF DESCRIPTION OF THE DRAWINGS

The foregoing and other aspects of embodiments of this invention are made more evident in the following Detailed Description, when read in conjunction with the attached Drawing Figures, wherein:

FIG. 3B shows improved features of a wireless electronic stethoscope in accordance with the example embodiments;

DETAILED DESCRIPTION

In this invention, we propose a novel wearable and non-wearable electronic stethoscopes with an improved configuration which uses digitized acoustic data for data analytics for listening, learning and interpreting acoustic data of a body.

A physician often uses a stethoscope to listen to the internal sounds of a human or animal body. Sounds come from heart, lung, intestines, arteries and veins. Abnormal sound is the first sign of a health issue. As the number of the aged people keeps increasing, the aged with chronic diseases also increase. However, the frequency of their visit to physicians may not be maintained due to a shortage of physicians and a cost burden to them. Another problem to the aged with chronic diseases is that even if they can see a physician regularly, such periodic checkups are not good enough to prevent heart failure or other acute life threatening exacerbation. The Watson Analytics system can learn and store the relationships between the digitized body sound data and the human (or animal) health conditions. It is expected that almost all aged people would have cell phones which can transmit the health data from a sensor to a server. Earlier warnings by electronic stethoscopes or wearable wireless stethoscopes can save the lives as well as maintain the quality of life, which may be especially beneficial for the aged people. The example embodiments of the invention work to address at least these needs.

Figure 1:
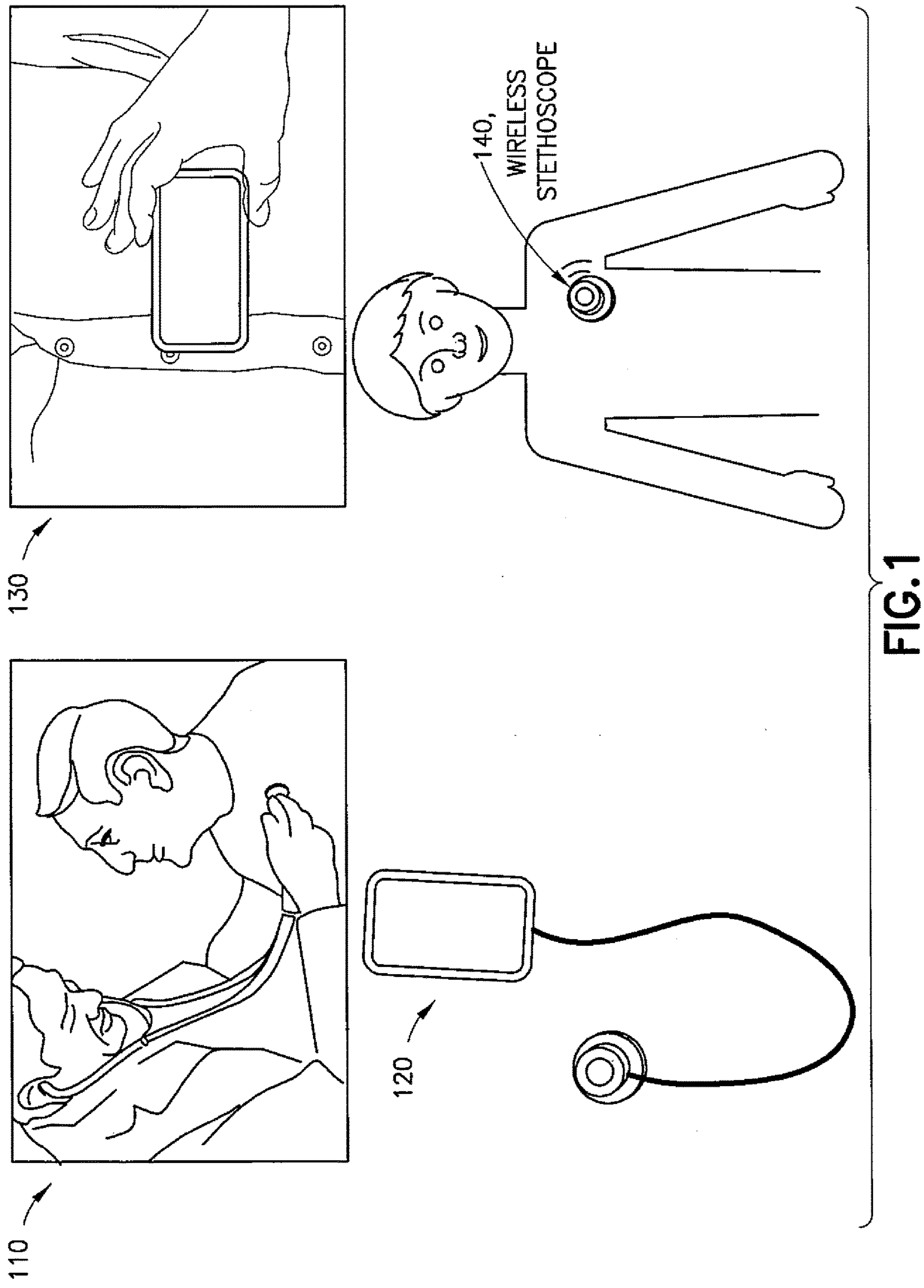
FIG. 1 shows several different stethoscope applications and a new wireless stethoscope application in accordance with the example embodiments of the invention.

With regards to FIG. 1 there is illustrated images relating to different types of stethoscope operations some of which can be used in accordance with the example embodiments. First, as shown in item 110 of FIG. 1 (top-left) there is a conventional stethoscope operation with a conventional stethoscope used by a doctor. As shown in item 110 the doctor examines a patient with the conventional stethoscope. In addition, as shown in in item 120 of FIG. 1 there is a stethoscope that has a physical connection to a smart phone which may be used to view acoustic data from the stethoscope. The wireless electronic stethoscope in accordance with the example embodiments of the invention is a substantial improvement over these conventional stethoscope applications.

For example, J. Ko, et al, "Wireless Sensor Networks for Healthcare", Proceedings of the IEEE, Vol 98, No 11, pp 1947-1960 (2010). S. Patel, et al, "A review of wearable sensors and systems with application in rehabilitation," J of NeuroEngr and Rehabilitation 2012, 9:21. These two papers describe (a) wireless sensor networks for healthcare and (b) wearable sensors for rehabilitation. But they did not describe wireless acoustic sensor as a stethoscope. Regarding U.S. Pat. Nos. 6,527,729 B1; 8,197,431 B2; U.S. 2004/0100376 A1; U.S. Pat. Nos. 7,724,147 B2; 6,498,854 B1; 6,661,897 B2; U.S. Patent 2004/0100376 A1; and U.S. Patent 2006/0018487 A1, these prior arts are seen to describe (a) monitoring heart failure & health conditions with acoustic sensors, (b) use of acoustic sensors for therapy, (c) a general wireless healthcare monitoring & notification systems, (d) biosensor for health monitoring, (e) transducer designs, (f) acoustic-to-electrical transducer for sensing body sounds, and (g) electronic stethoscope. However, none of these references have described (i) diagnosis of the digitized acoustic data with IT data analytics such as Watson Analytics, (ii) use of the analytics as an early warning system through cell phones, and (iii) wearable wireless stethoscopes.

Further, it is noted that commercial digital stethoscopes (e.g., item 120) such as those made by Thinklabs®, 3M Littman®, or Cardionics® may also be used for telemedicine, offering high-quality live listening, recording, storing and forwarding heart and lung sounds for all types of telemedicine applications. However, none of these commercial digital stethoscopes have been developed to additionally provide an early warning system with information technology analytics, such as IBM Watson Analytics.

For example, the wireless electronic stethoscope in accordance with the example embodiments of the invention is configured to communicate digitized health care data to a system, such as an IBM Watson Analytics system, in order to provide real-time diagnosis and warnings to the user of the stethoscope. Further, as shown in item 130 of FIG. 1 a wireless electronic stethoscope and/or wireless stethoscope application in accordance with the example embodiments is incorporated into a smart phone which is placed on a body to collect the body sounds and then transmit them wirelessly to the IBM Watson Analytics system. This is at least due to the novel construction of the wireless electronic stethoscope diaphragm making it thinner and more efficient. The wireless electronic stethoscope in accordance with the example embodiments of the invention has an improved design over conventional types of stethoscopes. The wireless communication functionality of the exemplary wireless electronic stethoscope will improve healthcare monitoring and provide improved functionality to a user. As will be discussed below the novel diaphragm can be combined with a Micro-Electro-Mechanical System (MEMS) microphone and installed in an electronic device such as the smart phone of item 130.

In addition, as shown in item 140 of FIG. 1 the wireless electronic stethoscope in accordance with the example embodiments is designed such that at least due to its size and configuration the stethoscope can be adhered onto a body for acoustic data sound collection and transmission. The size and weight of the wireless electronic stethoscope is such that the user can keep the stethoscope in place as long as needed without the stethoscope causing discomfort or being intrusive. Further, acoustic sounds from the wireless electronic stethoscope, in accordance with the example embodiments, transmitted, by the electronics of the wireless electronic stethoscope itself, to a server such as an IBM Watson Analytics server for real-time interpretation and a diagnosis.

Further, as similarly stated above, a wireless electronic stethoscope application in accordance with the example embodiments of the invention can be installed in a smart phone, such as other apps installed in smart phones. The wireless electronic stethoscope application can operate independently within a device such as a smart phone to obtain acoustic data from multiple spots of a person or an animal on which it is placed, and transmit digitized data representations of the obtained acoustic data to an IBM Watson Analytics server. In accordance with the example embodiments the IBM Watson Analytics server can function as a doctor of sorts, similar to the doctor as shown in item 110 of FIG. 1.

The example embodiments of the invention provide a wireless electronic stethoscope which includes a miniaturized electronic stethoscope and a radio frequency (RF) chip. The digitized acoustic data of body sounds are transmitted with the RF chip to a server such as IBM Watson Analytics server, which collects and analyzes the digitized data and then electronically informs the user of its diagnosis in real time.

The wireless electronic stethoscope in accordance with the example embodiments can be either wearable or non-wearable. The body contact area of the electronic stethoscope is made of human skin-compatible adhesive such ones used for medical tapes. Wearable and non-wearable healthcare sensors collect and transmit individual's health data to a Watson system, which, in turn, makes a diagnosis using its analytics and then sends the individual early diagnosis, instruction and/or warning in real time. The electronic stethoscope can be made of piezoelectric materials, MEMS, electromagnetic diaphragms, etc. The analytics can reduce noises and amplify the acoustic signals. The heath data which a wearable wireless electronic stethoscope in accordance with the example embodiments can ascertain and transmit include but are not limited to heart rate, pulse wave, blood pressure, temperature, hydration, blood $O_2$ level, respiratory rate, various organ sounds, movements, and rate of movements data. The heath data which a non-wearable wireless electronic stethoscope can ascertain and transmit include but are not limited to blood glucose, breathing, blood pressure, etc. data.

With regards to FIG. 2 there is shown features of a MicroElectro-Mechanical System (MEMS) microphone. The MEMS microphone as shown in FIG. 2 includes a perforated backplate with inserted electrodes placed over a diaphragm with support posts. The perforations provide acoustic ports for the back volume through the backplate. Also as shown in FIG. 2 the MEMS microphone system may be small, the size of a U.S. quarter. In accordance with the example embodiments the MEMS can be configured to operate with and/or incorporate with a wireless electronic stethoscope within an electronic device such as a smart phone. Further, it is noted that in accordance with the embodiments electronic circuitry including the RF chip can operate with a diaphragm associated with the MEMS to communicate acoustic data of a body to an IBM Watson Analytics server or alternate Cognitive computer or device.

Figure 2B:
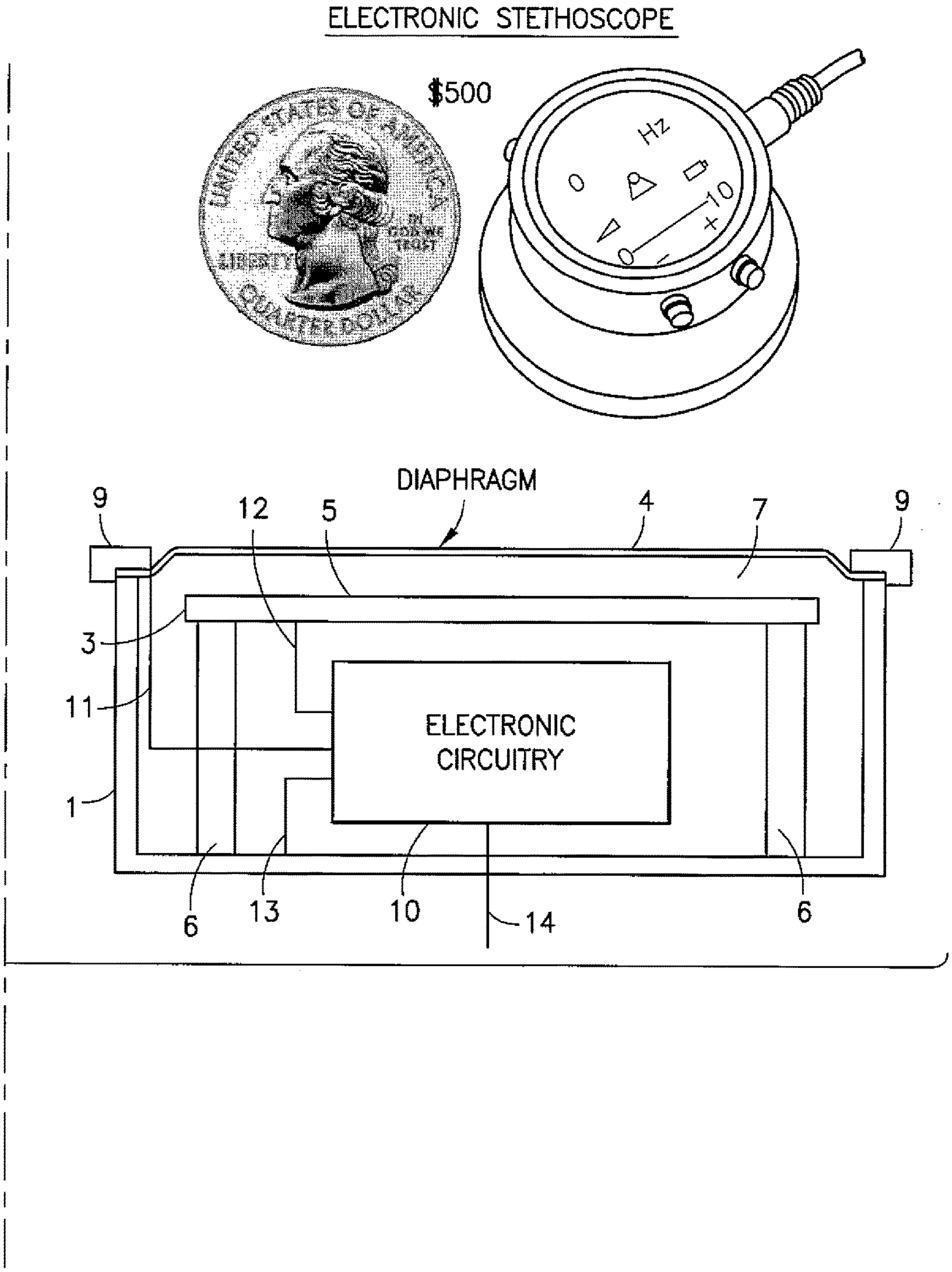
FIG. 2 includes FIG. 2A and FIG. 2B and shows a comparison between an MEMS microphone and an electronic stethoscope.

Also as shown in FIG. 2B of FIG. 2 there is a conventional electronic stethoscope which includes a diaphragm 4 over electronic circuitry 10. Remaining items 3, 5, 6, 7, 9, 11, 12, 13, and 14 of the electronic stethoscope of FIG. 2 are described as follows. In FIG. 2B, item 3 of the stethoscope shows a metal conductor baseplate; item 5 shows a mylar or polymer film; item 6 shows a housing of the stethoscope; item 7 shows a gap area; item 9 shows supports of the housing 6; items 11 and 12 show connections between the electronic circuitry 10 and the diaphragm 4; and item 13*s* show a connection between the electronic circuitry 10 and the housing 6; and item 14 shows a connection to the electronic circuitry 10, the connection 14 can be used at least for power and/or signaling for the electronic circuitry 10.

It is noted that either of the MEMS microphone or the stethoscope of FIG. 2B of FIG. 2 can be small, such as the size of a U.S. quarter as shown in FIG. 2A of FIG. 2. However, as also shown in FIG. 2A and FIG. 2B of FIG. 2, the costs of these devices can be very disparate. As shown in FIG. 2A of FIG. 2 the MEMS microphone system can cost only about ten U.S. dollars, whereas the cost of the electronic stethoscope system can cost upwards of five hundred U.S. dollars. The example embodiments of the invention take cost and size into account to provide novel wearable and non-wearable electronic stethoscopes with an improved diaphragm configuration which communicates digitized acoustic data for data analytics using an IBM Watson Analytics server.

Further, MEMS type sensors or microphones are widely used in modern smart phones. There are two different MEMS: capacitive and piezoelectric. It is noted that the MEMS microphone is also called a microphone chip or silicon microphone. A pressure-sensitive diaphragm is etched directly into a silicon wafer by MEMS processing techniques, and is usually accompanied with integrated preamplifier. In an example embodiment of the invention such a MEMS type sensor or microphone can be used by an exemplary wireless electronic stethoscope application to retrieve acoustic data to produce digitized data which is wirelessly sent to a server such as an IBM Watson Analytics server. The IBM Watson Analytics server receives and analyzes the data and then in real-time informs the person of any abnormal sound with a recommendation of seeing a person, such as a doctor with the problem-related specialty.

In another example embodiment, a miniaturized stethoscope equipped with the RF chip that can convert the acoustic data to the digitized data and then transmit the digitized data wirelessly to a smart phone and then to a server. The wireless electronic stethoscope in accordance with the example embodiments is configured to identify and select a specified body part so that the IBM Watson Analytics server can recognize the sounds of the specified body part for a diagnosis.

In another example embodiment, the data analytics of the IBM Watson Analytics server can establish a relationship between the digitized acoustic data from a certain body part and a health status of the body. Such analytics can be used for a diagnosis of a person or an animal in real time. In another embodiment, the contact area of the wireless electronic stethoscope is partially or entirely covered with a biocompatible pressure adhesive so that the stethoscope can be attached temporarily onto a part of a body. A typical biocompatible pressure adhesive is used for medical tapes.

In accordance with the example embodiments of the invention communication of data from one or more sensors, analysis of the data and communication of the result of analysis of the data can be done locally at or near the sensor, at or near a cognitive device and/or communication device such as a smart phone and/or at a remote data hub such as a home secure/encrypted communication data hub, a data center, a cloud computing data center or any combination of the hereto for locations for partial or complete data analysis, diagnostics alert, diagnostics trend or representation by any means to the user, healthcare professional, doctor, or other receiver of the results or recommendations.

In accordance with the example embodiments such as an alert, or trend of information or full diagnosis and actionable recommendation is communicated back to the user, healthcare professional, doctor and/or designated person and/or secure data storage location. In accordance with the example embodiments the digitized acoustic data can be computed at a local cognitive computer or device, such as a smart phone, tablet, or laptop, and the acoustic data and/or digitized acoustic data can be sent with security/encryption in full or in specific part to a smart phone, a home health care storage and/or computing hub.

In another example embodiment, a temperature sensor is incorporated in the wireless electronic stethoscope so that the device can recognize an appropriate contact to human or animal skins. Thus, the stethoscope is configured to turn on when touched to human skins. This turning on can also, or instead, be based on a proper versus improper placement of the stethoscope on the skin. A proper placement can be determined by a pre-determined minimum signal strength level and/or minimal resistance level through skin for example. To avoid a confusion between the human body temperature and the ambient temperature, the wireless electronic stethoscope can be configured to function only in a certain temperature range (e.g., from 30° C. to 40°).

Figure 3A:
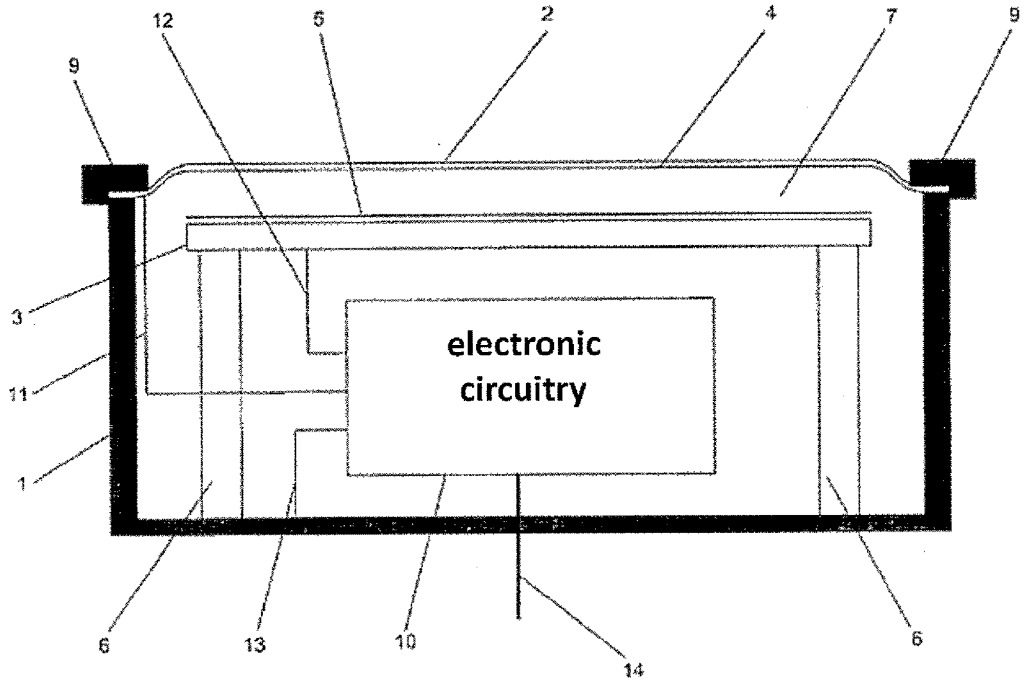
FIG. 3A shows features of a conventional electronic stethoscope.

FIG. 3A shows a conventional electronic stethoscope. As shown in FIG. 3A the conventional electronic stethoscope includes a diaphragm 2 which includes a thin metal conductor 4. The diaphragm 2 is secured by a diaphragm mount 9. Below the diaphragm 2 is Mylar (polymer) film 5 over a thin metal conductor plate 3. In the conventional electronic stethoscope a gap between the diaphragm 2 and the thin metal conductor plate 3 is greater than 100 um and includes air or liquid 7. Items 1 and 6 of FIG. 3A show a Cr-coated housing. In addition, the conventional electronic stethoscope of FIG. 3A includes electronic circuitry 10 including a wire to a battery 14. Also included in the conventional electronic stethoscope of FIG. 3A are electronic circuitry 11 and 13.

FIG. 3B illustrates a wireless electronic stethoscope in accordance with the example embodiments of the invention. As shown in FIG. 3B the wireless electronic stethoscope as shown in FIG. 3B, as compared to the conventional electronic stethoscope as shown in FIG. 2, includes new materials and electronics including a bio-compatible pressure adhesive 21; a thin polymer film 22; elastomeric pyramids 23 (5-20 um gap); new electronic circuitry 24 which provides capacitance measurement, capacitance to digital converter, amplifier, and radio frequency (RF) signaling; as well as a battery 25. All of which is housed in a thinner stethoscope 26.

Figure 4:
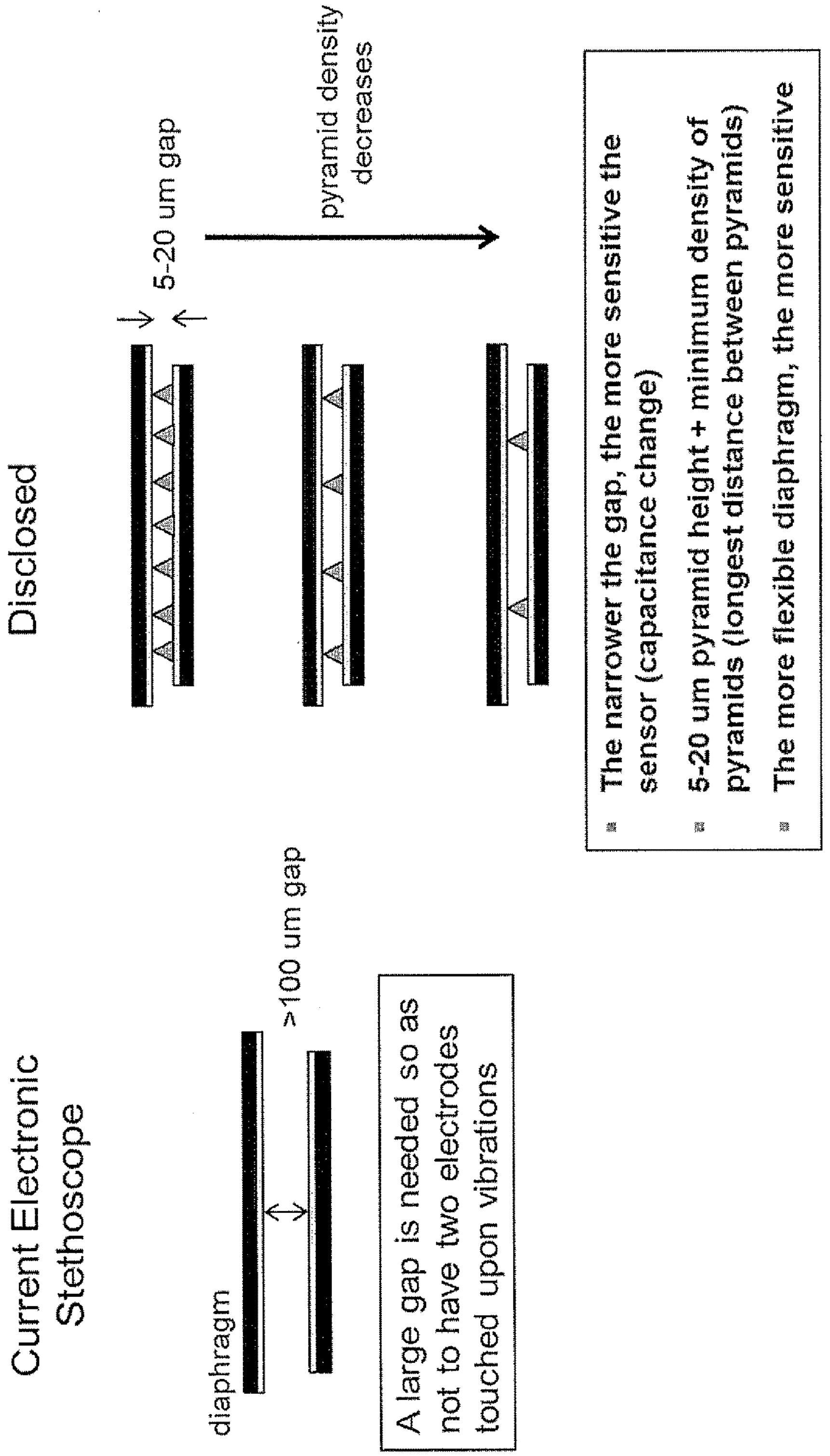
FIG. 4 shows example embodiment electronic stethoscope configuration and electronics as compared to a current or conventional electronic stethoscope configuration.

In FIG. 4 there is shown a clear distinctions between a wireless electronic stethoscope, as in accordance with the example embodiments of the invention, and a conventional electronic stethoscope. These distinctions relate to improvements in use and function of the conventional stethoscope. As shown on the left side of FIG. 4, a diaphragm of the current or conventional electronic stethoscope includes a large gap, e.g., a 100 um gap, between electrodes of the diaphragm. Whereas, the electronic stethoscope of the example embodiments as shown on the right side of FIG. 4 under the heading “Disclosed” has only a 5-20 um gap between the diaphragm and the metal conductor plate. In accordance with the example embodiments as shown in FIG. 4 there are elastomeric pyramids, as also shown in FIG. 3B, between the diaphragm and the metal conductor plate. In accordance with the example embodiments these elastomeric pyramids enable the gap between the diaphragm and the metal conductor plate to be much smaller than the conventional or current stethoscopes. The narrower the gap between the diaphragm and the metal plate the more sensitive the sensor is due at least to a capacitance change. In addition, in accordance with the example embodiments of the invention a density and/or a height of the elastomeric pyramids between the diaphragm and the metal conductor plate is configured to provide increased sensitivity. The density of the elastomeric pyramids is determined by a distance between different elastomeric pyramids and/or a number of the elastomeric pyramids between the diaphragm and the metal conductor plate. The configuration of the distance and height of the different elastomeric pyramids can change the flexibility of the diaphragm.

According the embodiments, for different application purposes the pyramid population may be decreased by increasing the distance or gap between neighboring pyramids. In accordance with the example embodiments of the invention sensitivity and flexibility of the stethoscope can be increased as the gap is narrowed further in the 5 to 20 um range and the density of the elastomeric pyramids is decreased. The density of the elastomeric pyramids can be configured using two or more pyramids. In accordance with the example embodiments a distance (or gap) between the apexes of any two pyramids can be up to 100 times the height of a pyramid. Further, in accordance with the embodiments a base width of a pyramid depends on the height, or vice versa.

It is further noted that elastomeric pyramids are made using an elastomer solution such as a Polydimethylsiloxane (PDMS) solution and a mold such as silicon 100. For example, the pyramid cab be a silicon wafer etched with a potassium hydroxide (KOH) solution to yield reverse pyramid pits. Then a solution of PDMS is spin-coated onto the etched silicon wafer mold followed by curing the PDMS. The cured solid PDMS is pulled out of the silicon wafer mold to get the PDMS pyramids. The pyramid side-wall angle of 54.7 degree forms when the silicon is etched with KOH due to the different etch rates in the different silicon crystallographic planes in KOH.

Further, it is noted that for at least reasons of medical data security, programing as well as signaling of the wireless electronic stethoscope in accordance with the example embodiments may be deployed, accessed and executed with the electronic circuitry 24 through the use of a virtual private network (VPN), which is any combination of technologies that can be used to secure a connection through an otherwise unsecured or untrusted network. The VPN makes use of a private network and/or a public network, usually the Internet, to connect the wireless electronic stethoscope and the analytics server together. Instead of using a dedicated, real-world connection such as leased line, the VPN uses "virtual" connections routed through the Internet from the user's or associates private network to the remote site which houses the server. Access to the software updates for the stethoscope via a VPN can be provided as a service by a server, such as the analytics server, by specifically constructing the VPN for purposes of delivery or execution of the process software or signaling of the electronic stethoscope in accordance with the example embodiments (i.e., the software resides elsewhere). The process software may be deployed, accessed, and executed through the VPN by the server or the user of the stethoscope. The update software is transported over the VPN via tunneling, which is the process of placing an entire packet within another packet and sending it over a network.

Figure 5:
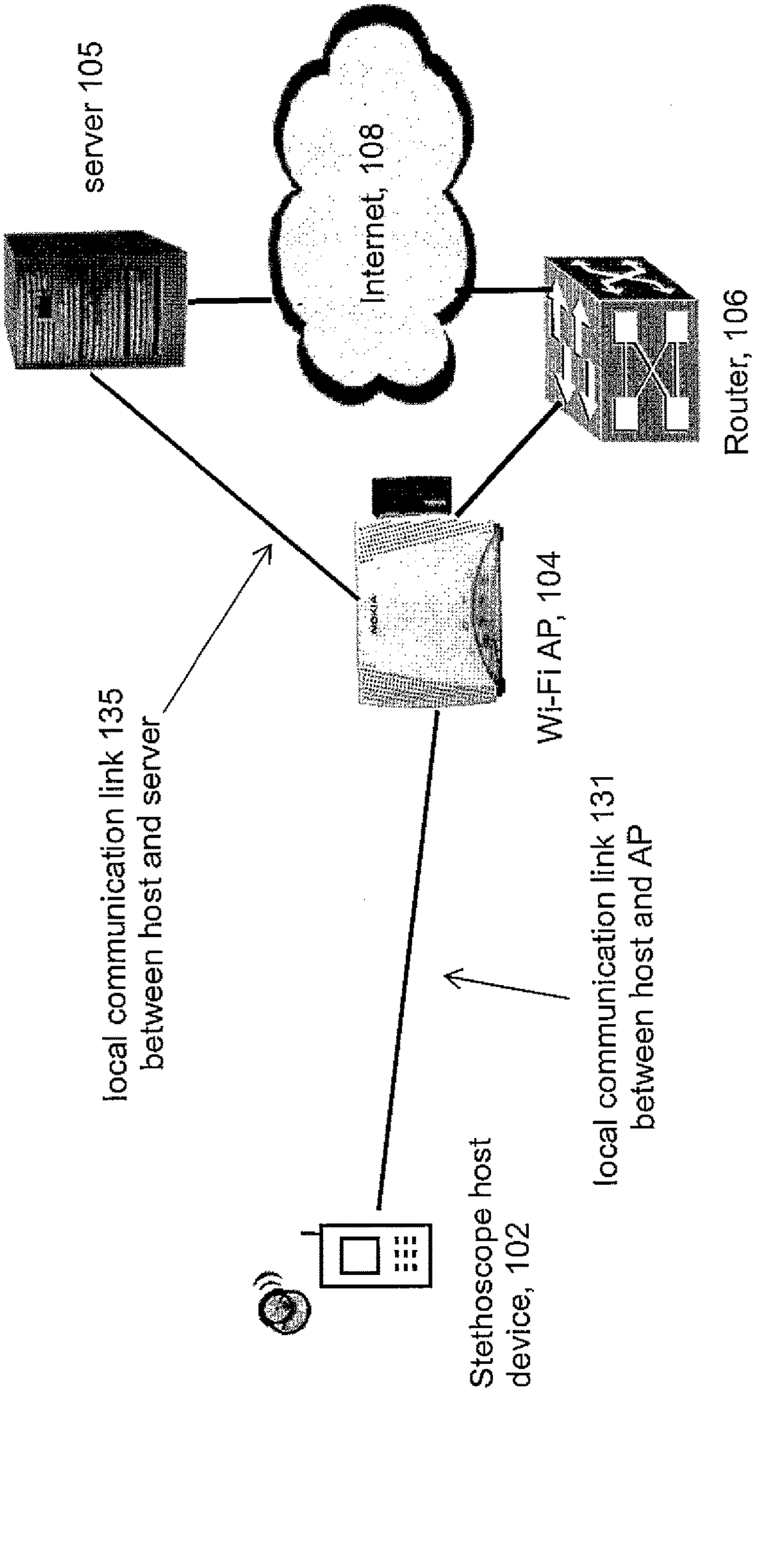
FIG. 5 is a schematic representation showing communication links between a wireless electronic stethoscope host device in accordance with the example embodiments and any of several nodes of an access network such as a Wi-Fi network.

FIG. 5 schematically illustrates possible communication scenarios which may be utilized for communication between the wireless stethoscope and an IBM Watson Analytics server in accordance with the example embodiments of the invention. Shown are the stethoscope host device 102, the AP 104, and a separate server 105 may or may not be co-located with the AP 104 or the router 106. It is noted that the illustration of a stethoscope host device 102 including a stethoscope and a phone as in FIG. 5 is not limiting to the invention. In accordance with the example embodiments the stethoscope host device 102 can represent a wireless electronic stethoscope by itself, a wireless electronic stethoscope in communication with a host device such as a smart phone, or a wireless stethoscope application loaded on a device such as a smart phone. In a first case assume that the AP 104, router 106 and server 105 illustrated at FIG. 5 are all part of or are co-located with the Wi-Fi/WLAN access network. The stethoscope host device 102 may access the server 105 via the local communication link is as shown by reference number 131 to the Wi-Fi AP 104, and the local communication link 135 to the server 105. For another case in which the server 105 is not part of or is not co-located with the Wi-Fi/WLAN access network, the stethoscope host device 102 may access the server 105 via the local communication link is as shown by reference number 131 to the Wi-Fi AP 104, and then to the router 106, and the Internet where from the separate server 105 may be accessed.

In accordance with the example embodiments the stethoscope host device 102 can initiate a connection to communication port number X using the link-local address of the node at which the local link terminates, such as the server 105, the AP 104, or the router 106. The stethoscope host device 102 knows or discovers this port number X through appropriate mechanisms, such as by selection of a default port, DHCP, or layer 2 signaling, as detailed above. In return, the server 105 sends a connection accept message back to the stethoscope host device 102. At this juncture the local communication link has been established between the stethoscope host device 102 and the server 105 of the access network. Next the stethoscope host device 102 can initiate a VPN connection at message exchange. Such initiation is done conventionally with the network for which the stethoscope host device 102 may use an appropriate username and digital authentication keys. In accordance with the example embodiments the stethoscope host device 102 may communicate, via communications link such as the local communication link 135 and 131, digitized data from the acoustic data of the living body to an analytics system such as IBM Watson Analytics system running on the server 105.

Figure 6:
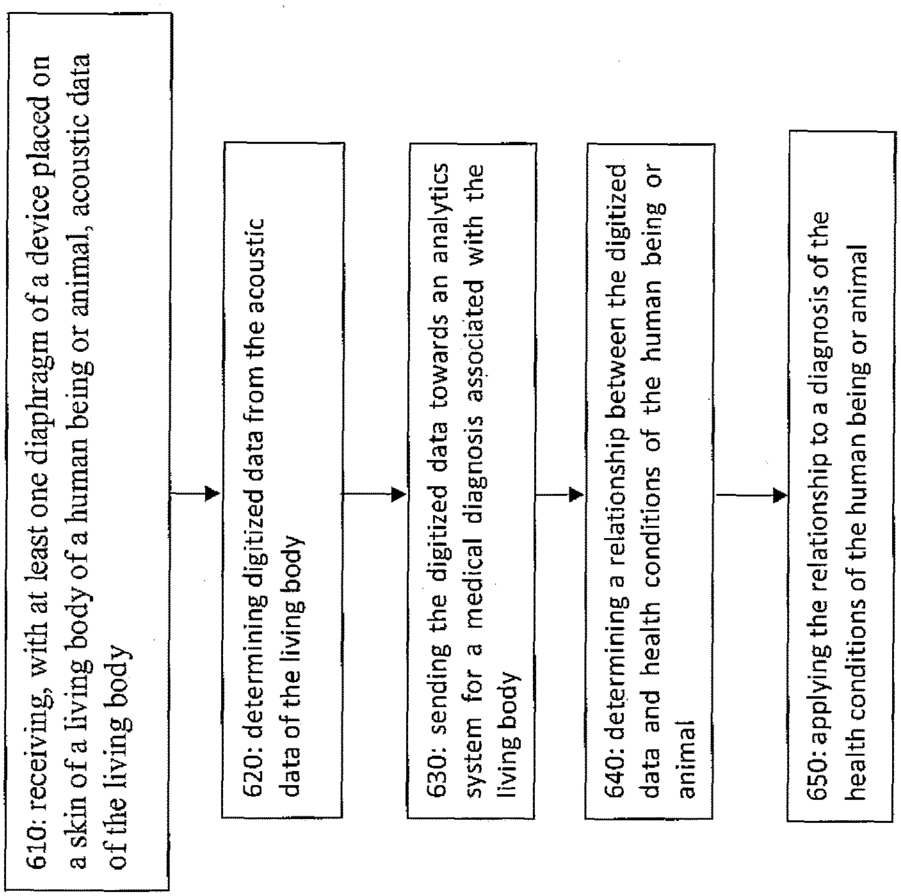
FIG. 6 shows a method in accordance with the example embodiments of the invention which may be performed by an apparatus.

FIG. 6 shows a method in accordance with the exemplary embodiments which may be performed by an apparatus.

FIG. 6 illustrates operations which may be performed by a device such as, but not limited to, a wired or wireless electronic stethoscope device (e.g., as in FIG. 3). As shown in step 610 of FIG. 6, there is receiving, with at least one diaphragm of a device placed on a skin of a living body of a human being or animal, acoustic data of the living body; at step 620 of FIG. 6 there is determining digitized data from the acoustic data of the living body; at step 630 pf FIG. 6 there is sending the digitized data towards an analytics system for a medical diagnosis associated with the living body; at step 640 there is determining a relationship between the digitized data and health conditions of the human being or animal; and at step 650 there is applying the relationship to a diagnosis of the health conditions of the human being or animal.

In accordance with the exemplary embodiments as described in the paragraph above, the at least one diaphragm is placed over elastomer pyramids set on a metal conductor plate.

In accordance with the exemplary embodiments as described in the paragraphs above, the elastomer pyramids have a height of 5-20 micro meters.

In accordance with the exemplary embodiments as described in the paragraphs above, the elastomer pyramids have a predetermined spacing between them.

In accordance with the exemplary embodiments as described in the paragraph above, the predetermined spacing between the elastomer pyramids can be up to one hundred times a height of a pyramid shaped structure.

In accordance with the exemplary embodiments as described in the paragraphs above, the predetermined spacing is changed to one of increase or decrease a sensitivity of the at least one diaphragm to receive the acoustic data.

In accordance with the exemplary embodiments as described in the paragraphs above, the predetermined spacing comprises the elastomer pyramids are spaced farther apart to increase the sensitivity of the at least one diaphragm.

In accordance with the exemplary embodiments as described in the paragraphs above, the at least one diaphragm is covered with a polymer film which can be replaced with another film of the same materials so that the adhesive and hygienic conditions can be refreshed.

In accordance with the exemplary embodiments as described in the paragraphs above, the polymer film comprises a biocompatible pressure adhesive to adhere the device to the skin of the living body.

In accordance with the exemplary embodiments as described in the paragraphs above, the at least one diaphragm is placed on the skin of the body at one of a wrist, ankle, or other location of the body using one of a variable elastic band or pressure bladder.

In accordance with the exemplary embodiments as described in the paragraphs above, the device comprises electronic circuitry which provides capacitance measurement, a capacitance to digital converter, an amplifier for the determining the digitized data.

In accordance with the exemplary embodiments as described in the paragraphs above, the electronic circuitry comprises circuitry for radio frequency signaling the digitized data towards an analytics system.

In accordance with an example embodiment of the invention as described above there is an apparatus comprising: means for receiving with at least one diaphragm of a device (e.g., wireless electronic stethoscope device of FIG. 3B) placed on a skin of a living body of a human being or animal, acoustic data of the living body; means for determining digitized data from the acoustic data of the living body; means for sending the digitized data towards an analytics system for a medical diagnosis associated with the living body; means for determining a relationship between the digitized data and health conditions of the human being or animal; and means for applying the relationship to a diagnosis of the health conditions of the human being or animal.

In accordance with the example embodiments of the invention, the electronic circuitry 24 of the wireless stethoscope can include a computer program product. The computer program product may include or be connected to a computer readable storage medium (or media) having computer readable program instructions thereon for causing a processor of the electronic circuitry 24 to carry out aspects of the present invention. The computer readable storage medium can be a tangible device that can retain and store instructions for use by an instruction execution device. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic connection), or electrical signals transmitted through a wire. Computer readable program instructions described herein can be downloaded to respective electronic circuitry 24 of a stethoscope from a computer readable storage medium or to an external computer or external storage device via a network, for example, the Internet, a local area network, a wide area network and/or a wireless network. Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages.

It should be noted that the terms "connected," "coupled," or any variant thereof, mean any connection or coupling, either direct or indirect, between two or more elements, and may encompass the presence of one or more intermediate elements between two elements that are "connected" or "coupled" together. The coupling or connection between the elements can be physical, logical, or a combination thereof. As employed herein two elements may be considered to be "connected" or "coupled" together by the use of one or more wires, cables and/or printed electrical connections, as well as by the use of electromagnetic energy, such as electromagnetic energy having wavelengths in the radio frequency region, the microwave region and the optical (both visible and invisible) region, as several non-limiting and non-exhaustive examples.

Furthermore, some of the features of the preferred embodiments of this invention could be used to advantage without the corresponding use of other features. As such, the foregoing description should be considered as merely illustrative of the principles of the invention, and not in limitation thereof.

What is claimed is:

1. A method comprising:

receiving, with at least one diaphragm of a device placed on a skin of a living body, acoustic data of the living body, wherein the at least one diaphragm is covered with a polymer film, and wherein the at least one diaphragm is placed over elastomer pyramids set on a metal conductor plate;

determining digitized data from the acoustic data of the living body of a human being or animal;

sending the digitized data towards an analytics system for a medical diagnosis associated with the living body;

determining a relationship between the digitized data and health conditions of the human being or animal; and applying the relationship to a diagnosis of the health conditions of the user of the acoustic device.

2. The method according to claim 1, wherein the elastomer pyramids have a height of 5-20 micro meters.

3. The method according to claim 1, wherein the elastomer pyramids have a predetermined spacing between them, wherein the predetermined spacing is up to one hundred times a height of the elastomer pyramids.

4. The method according to claim 3, wherein the predetermined spacing is changed to one of increase or decrease a sensitivity of the at least one diaphragm to receive the acoustic data.

5. The method according to claim 3, wherein the predetermined spacing comprises the elastomer pyramids are spaced farther apart to increase the sensitivity of the at least one diaphragm.

6. The method according to claim 1, wherein the polymer film is replaced with another film of the same materials to refresh adhesive and hygienic conditions of the device.

7. The method according to claim 1, wherein the polymer film comprises a biocompatible pressure adhesive to adhere the device to the skin of the living body.

8. The method according to claim 1, wherein the device comprises electronic circuitry which provides capacitance measurement, a capacitance to digital converter, an amplifier for the determining the digitized data.

9. The method according to claim 1, wherein the electronic circuitry comprises circuitry for radio frequency signaling the digitized data towards an analytics system.

10. An apparatus comprising: at least one processor; and at least one memory including computer program code, where the at least one memory and the computer program code are configured, with the at least one processor, to cause the apparatus to at least:

receive, with at least one diaphragm of the apparatus placed on a skin of a living body, acoustic data of the living body, wherein the at least one diaphragm is covered with a polymer film, and wherein the at least one diaphragm is placed over elastomer pyramids set on a metal conductor plate;

determine digitized data from the acoustic data of the living body of a human being or animal; and send the digitized data towards an analytics system for a medical diagnosis associated with the living body;

determine a relationship between the digitized data and health conditions of the human being or animal; and apply the relationship to a diagnosis of the health conditions of the human being or animal.

11. The apparatus according to claim 10, wherein the elastomer pyramids have a height of 5-20 micro meters.

12. The apparatus according to claim 10, wherein the elastomer pyramids have a predetermined spacing between them, wherein the predetermined spacing is up to one hundred times a height of the elastomer pyramids.

13. The apparatus according to claim 12, wherein the predetermined spacing is changed to one of increase or decrease a sensitivity of the at least one diaphragm to receive the acoustic data, and wherein the predetermined spacing comprises the elastomer pyramids are spaced farther apart to increase the sensitivity of the at least one diaphragm.

14. The apparatus according to claim 10, wherein the at least one diaphragm is placed on the skin of the body at one of a wrist, ankle, or other location of the body using one of a variable elastic band or pressure bladder.

15. The apparatus according to claim 10, wherein the polymer film is replaced with another film of the same materials to refresh adhesive and hygienic conditions of the apparatus.

16. The apparatus according to claim 10, wherein the polymer film comprises a biocompatible pressure adhesive to adhere the apparatus to the skin of the living body.

17. The apparatus according to claim 10, wherein the apparatus comprises electronic circuitry which provides capacitance measurement, a capacitance to digital converter, an amplifier for the determining the digitized data.

18. The apparatus according to claim 17, wherein the electronic circuitry comprises circuitry for radio frequency signaling the digitized data towards an analytics system.

* * * * *